United States Patent

Siegle et al.

[11] 3,980,673
[45] Sept. 14, 1976

[54] CERTAIN 2,3-DIHYDROBENZOFURANYL ESTERS OF CERTAIN N-SULFENYLATED CARBAMIC ACIDS

[75] Inventors: Peter Siegle, Cologne; Engelbert Kühle, Bergedorf-Gladbach; Ingeborg Hammann, Cologne; Wolfgang Behrenz, Overath-Steinenberuck; Bernhard Homeyer, Opladen, all of Germany

[73] Assignee: Bayer Aktiengesellschaft, Leverkusen, Germany

[22] Filed: Aug. 19, 1974

[21] Appl. No.: 498,675

[30] Foreign Application Priority Data

Sept. 1, 1973 Germany............................ 2344175

[52] U.S. Cl. .......................... 260/346.2 R; 424/285
[51] Int. Cl.[2] ........................................ C07D 307/86
[58] Field of Search ............................ 260/346.2 R

[56] References Cited
UNITED STATES PATENTS 3,847,951  11/1974  Kohn et al. ................. 260/346.2 R

FOREIGN PATENTS OR APPLICATIONS 710,959  2/1971  South Africa

*Primary Examiner*—Natalie Trousof
*Assistant Examiner*—Bernard Dentz
*Attorney, Agent, or Firm*—Burgess, Dinklage & Sprung

[57] ABSTRACT

N-sulfenylated 2,3-dihydrobenzofuranyl-7-N-methylcarbamates of the formula

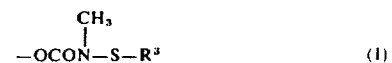

in which
 R[1] is hydrogen or $C_1$–$C_6$ alkyl,
 R[2] is $C_1$–$C_6$ alkyl, and
 R[3] is phenyl; phenyl substituted by at least one of halogen, $C_1$–$C_6$ alkyl and trihalogenomethyl; methoxycarbonyl; or the radical

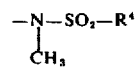

wherein
 R[4] is alkylamino, dialkylamino, phenyl, or phenyl substituted by at least one of halogen, $C_1$–$C_6$ alkyl or trihalogenomethyl,
which possess insecticidal and acaricidal properties.

4 Claims, No Drawings

CERTAIN 2,3-DIHYDROBENZOFURANYL ESTERS OF CERTAIN N-SULFENYLATED CARBAMIC ACIDS

The present invention relates to and has for its objects the provision of particular new N-sulfenylated 2,3-dihydrobenzofuranyl-7-N-methylcarbamates, which possess insecticidal or acaricidal properties, active compositions in the form of mixtures of such compounds with solid and liquid dispersible carrier vehicles, and methods for producing such compounds and for using such compounds in a new way especially for combating pests, e.g. insects and acarids, with other and further objects becoming apparent from a study of the within specification and accompanying examples.

It has already been disclosed that carbamates possess pesticidal properties. The best-known representatives of this class are the active compounds o-isopropoxyphenylcarbamate (Compound A) and α-naphthylcarbamate (Compound B), which are used as commercial products. However, the activity of these compounds is not always satisfactory, especially if low concentrations are used.

Further, it has been disclosed in German Published Specification DOS No. 1,922,929 that trihalogenomethylsulfenylated N-methyl-carbamic acid aryl esters are very good insecticides and that they are superior compared to the unsubstituted carbamates because of the greater insecticidal activity and their lower toxicity to warm-blooded animals. However, the disadvantage of these compounds is that they frequently exhibit a skin-irritant action, which prevents their technical utilization in many fields.

The present invention provides, as new compounds, the N-sulfenylated 2,3-dihydrobenzofuranyl-7-N-methylcarbamates of the general formula

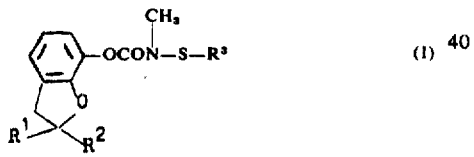

in which
R¹ is hydrogen or $C_1$–$C_6$ alkyl,
R² is $C_1$–$C_6$ alkyl, and
R³ is phenyl; phenyl substituted by at least one of halogen, $C_1$–$C_6$ alkyl and trihalogenomethyl; methoxycarbonyl; or the radical

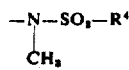

wherein
R⁴ is alkylamino, dialkylamino, phenyl, or phenyl substituted by at least one of halogen, $C_1$–$C_6$ alkyl or trihalogenomethyl.

Preferably, R¹ is hydrogen or methyl, R² is methyl, and R³ is phenyl, p-chlorophenyl, p-tolyl, m-trifluoromethylphenyl, 3,4-dichlorophenyl, N,N',N'-trimethylsulfonyldiamide, N-methylbenzenesulfonamide, N-methyl-3-trifluoromethylbenzenesulfonamide, N-methyl-4-chlorobenzenesulfonamide or N-methyl-4-toluenesulfonamide.

It is distinctly surprising that the compounds according to the invention exhibit a greater insecticidal, acaricidal and soil-insecticidal action than the commercially available carbamates o-isopropoxyphenylcarbamate and α-naphthylcarbamate. It is also surprising that the compounds according to the invention are substantially better tolerated by the skin than the known trihalogenomethylsulfenylated carbamic acid esters. The compounds according to the invention thus represent a real enrichment of the art.

The present invention also provides a process for the preparation of a sulfenylated compound of the formula (I), in which (a) a sulfenylated carbamic acid fluoride of the general formula

in which
R³ has the above-mentioned meaning, is reacted in the presence of a diluent, with a compound of the general formula

in which
R¹ and R² have the above-mentioned meanings, the latter being used as such, in the presence of an acid-binding agent, or in the form of an alkali metal salt thereof, or (b) a sulfenyl-chloride of the general formula

in which
R³ has the above-mentioned meaning, is reacted with a carbamate of the general formula

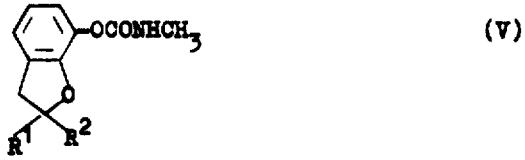

in which
R¹ and R² have the above-mentioned meanings, in the presence of a diluent and of an acid-binding agent.

If N-methyl-N-phenylmercaptocarbamic acid fluoride and 2,2-dimethyl-2,3-dihydro-benzofuranol-(7) are used, the course of the reaction can be represented by the following equation:

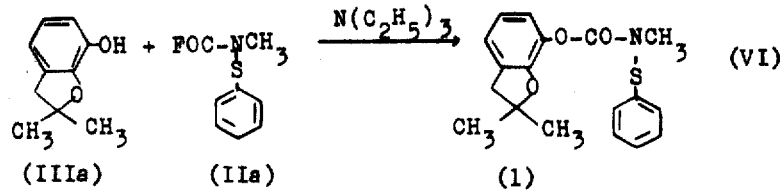

If phenylsulphenyl chloride and [2,2-dimethyl-2,3-dihydro-benzofuranyl-(7)]-N-methylcarbamate are used, the course of the reaction can be represented by the following equation:

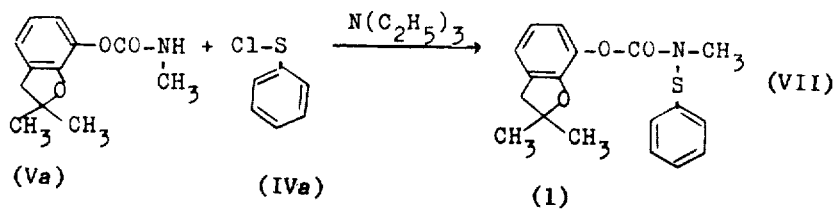

Sulfenylated carbamic acid fluorides of the formula (II) are known. They can be prepared according to the process of German Published Specification DAS No. 1,297,095 from the corresponding sulfenic acid chlorides, which are known, by reaction with the corresponding known N-mono-substituted carbamic acid fluorides.

The 2,3-dihydrobenzofuranyl-N-methylcarbamates to be used as starting products are known.

The diluents which can be used are all inert organic solvents. These include ethers, such as diethyl ether, dioxane and tetrahydrofuran, hydrocarbons, such as benzene, and chlorinated hydrocarbons, such as chloroform and chlorobenzene.

To bind the hydrogen halide liberated in the reaction, an acid-binding agent, preferably a tertiary organic base such as triethylamine, is added to the reaction mixture. It is optionally also possible to start directly from the alkali metal salts of the compounds of the formula (III).

The reaction temperature can be varied over a fairly wide range; in general, the reaction is carried out at between 0° and 100°C, preferably at from 20° to 40°C.

In carrying out the process according to the invention, equimolar amounts of the reactants may be used in general. In many cases, however, it has proved advantageous in process variant (a) to use the compound of the formula (III) in a slight excess. Preferably, 1.2 moles of benzofuranol of the formula (III) are employed per mole of the carbamic acid fluoride of the formula (II).

As already mentioned, the new N-sulfenylated 2,3-dihydrobenzofuranyl-7-N-methylcarbamates are distinguished by an outstanding insecticidal and acaricidal activity, especially against plant pests and pests harmful to health. They can also be used as fungicides. The compounds according to the invention are further distinguished by their low toxicity to warm-blooded animals, compared to the nonsulfenylated carbamates on which the compounds according to the invention are based.

The present compounds can therefore be employed particularly advantageously for combating sucking and biting insects, including pests harmful to health and pests of stored products, as well as soil insects and mites and phytopathogenic fungi. Furthermore, they possess a nematicidal and microbistatic action.

To the sucking insects there belong, in the main, aphids (Aphididae) such as the green peach aphid (*Myzus persicae*), the bean aphid (*Doralis fabae*), the bird cherry aphid (*Rhopalosiphum padi*), the pea aphid (*Macrosiphum pisi*) and the potato aphid (*Macrosiphum solanifolii*), the currant gall aphid (*Cryptomyzus korschelti*), the rosy apple aphid (*Sappaphis mali*), the mealy plum aphid (*Hyalopterus arundinis*) and the cherry black-fly (*Myzus cerasi*); in addition, scales and mealybugs (Coccina), for example the oleander scale (*Aspidiotus hederae*) and the soft scale (*Lecanium hesperidum*) as well as the grape mealybug (*Pseudococcus maritimus*); thrips (Thysanoptera), such as *Hercinothrips femoralis*, and bugs, for example the beet bug (*Piesma quadrata*), the red cotton bug (*Dysdercus intermedius*), and bed bug (*Cimex lectularius*), the assassin bug (*Rhodnius prolixus*) and Chagas' bug (*Triatoma infestans*) and, further, cicadas, such as *Euscelis bilobatus* and *Nephotettix bipunctatus*.

In the case of the biting insects, above all there should be mentioned butterfly caterpillars (Lepidoptera) such as the diamond-back moth (*Plutella maculipennis*), the gypsy moth (*Lymantria dispar*), the brown-tail moth (*Euproctis chrysorrhoea*) and tent caterpillar (*Malacosoma neustria*); further, the cabbage moth (*Mamestra brassicae*) and the cutworm (*Agrotis segetum*), the large white butterfly (*Pieris brassicae*), the small winter moth (*Cheimatobia brumata*), the green oak tortrix moth (*Tortrix viridana*), the fall armyworm (*Laphygma frugiperda*) and cotton worm (*Prodenia litura*), the ermine moth (*Hyponomeuta padella*), the Mediterranean flour moth (*Ephestia kühniella*) and greater wax moth (*Galleria mellonella*).

With the mites (Acarina) there are classed, in particular, the spider mites (Tetranychidae) such as the two-spotted spider mite (*Tetranychus urticae*) and the European red mite (*Paratetranychus pilosus = Panonychus ulmi*), gall mites, for example the blackcurrant gall mite (*Eriophyes ribis*) and tarsonemids, for example the broad mite (*Hemitarsonemus latus*) and th cyclamen mite (*Tarsonemus pallidus*); finally, ticks, such as the relapsing fever tick (*Ornithodorus moubata*).

When applied against pests harmful to health and pests of stored products, particularly flies and mosquitoes, the novel products are also distinguished by an outstanding residual activity on wood and clay, as well as a good stability to alkali on limed substrates.

The active compounds according to the instant invention can be utilized, if desired, in the form of the usual formulations or compositions with conventional inert (i.e. plant compatible or herbicidally inert) pesticide diluents or extenders, i.e. diluents, carriers or extenders of the type usable in conventional pesticide formulations or compositions, e.g. conventional pesticide dispersible carrier vehicles such as gases, solutions, emulsions, suspensions, emulsifiable concentrates, spray powders, pastes, soluble powders, dusting agents, granules, etc. These are prepared in known manner, for instance by extending the active compounds with conventional pesticide dispersible liquid diluent carriers and/or dispersible solid carriers optionally with the use of carrier vehicle assistants, e.g. conventional pesticide surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperatures and pressures, such as freon; inert dispersible liquid diluent carriers, including inert organic solvents, such as aromatic hydrocarbons (e.g. benzene, toluene, xylene, alkyl naphthalenes, etc.), halogenated, especially chlorinated, aromatic hydrocarbons (e.g. chlorobenzenes, etc.), cycloalkanes (e.g. cyclohexane, etc.), paraffins (e.g. petroleum or mineral oil fractions), chlorinated aliphatic hydrocarbons (e.g. methylene chloride, chloroethylenes, etc.), alcohols (e.g. methanol, ethanol, propanol, butanol, glycol, etc.) as well as ethers and esters thereof (e.g. glycol monomethyl ether, etc.), amines (e.g. ethanolamine, etc.), amides (e.g. dimethyl formamide, etc.), sulfoxides (e.g. dimethyl sulfoxide, etc.), acetonitrile, ketones (e.g. acetone, methyl ethyl ketone methyl isobutyl ketone, cyclohexanone, etc.). and/or water; as well as inert dispersible finely divided solid carriers, such as ground natural minerals (e.g. kaolins, clays, alumina, silica, chalk, i.e. calcium carbonate, talc, attapulgite, montmorillonite, kieselguhr, etc.) and ground synthetic minerals (e.g. highly dispersed silicic acid, silicates, e.g. alkali silicates, etc.); whereas the following may be chiefly considered for use as conventional carrier vehicle assistants, e.g. surface-active agents, for this purpose: emulsifying agents, such as non-ionic and/or anionic emulsifying agents (e.g. polyethylene oxide esters of fatty acids, polyethylene oxide ethers of fatty alcohols, alkyl sulfates, alkyl sulfonates, aryl sulfonates, albumin hydrolysates, etc., and especially alkyl arylpolyglycol ethers, magnesium stearate, sodium oleate, etc.); and/or dispersing agents, such as lignin, sulfite waste liquors, methyl cellulose, etc.

Such active compounds may be employed alone or in the form of mixtures with one another and/or with such solid and/or liquid dispersible carrier vehicles and/or with other known compatible active agents, especially plant protection agents, such as other insecticides and acaricides, or rodenticides, fungicides, bactericides, nematocides, herbicides, fertilizers, growth-regulating agents, etc., if desired, or in the form of particular dosage preparations for specific application made therefrom, such as solutions, emulsions, suspensions, powders, pastes, and granules which are thus ready for use.

As concerns commercially marketed preparations, these generally contemplate carrier composition mixtures in which the active compound is present in an amount substantially between about 0.1–95% by weight, and preferably 0.5–90% by weight, of the mixture, whereas carrier composition mixtures suitable for direct application or field application generally contemplate those in which the active compound is present in an amount substantially between about 0.0001–10%, preferably 0.01–1%, by weight of the mixture. Thus, the present invention contemplates over-all compositions which comprise mixtures of a conventional dispersible carrier vehicle such as (1) a dispersible inert finely divided carrier solid, and/or (2) a dispersible carrier liquid such as an inert organic solvent and/or water preferably including a surface-active effective amount of a carrier vehicle assistant, e.g. a surface-active agent, such as an emulsifying agent and/or a dispersing agent, and an amount of the active compound which is effective for the purpose in question and which is generally between about 0.0001–95%, and preferably 0.01–95%, by weight of the mixture.

The active compounds can also be used in accordance with the well known ultra-low-volume process with good success, i.e. by applying such compound if normally a liquid, or by applying a liquid composition containing the same, via very effective atomizing equipment, in finely divided form, e.g. average particle diameter of from 50–100 microns, or even less, i.e. mist form, for example by airplane crop spraying techniques. Only up to at most about a few liters/hectare are needed, and often amounts only up to about 15 to 1000 g/hectare, preferably 40 to 600 g/hectare, are sufficient. In this process it is possible to use highly concentrated liquid compositions with said liquid carrier vehicles containing from about 20 to about 95% by weight of the active compound or even the 100% active substance alone, e.g. about 20–100% by weight of the active compound.

Furthermore, the present invention contemplates methods of selectively killing, combating or controlling pests, e.g. insects and acarids, which comprises applying to at least one of correspondingly (a) such insects, (b) such acarids, and (c) the corresponding habitat thereof, i.e. the locus to be protected, e.g. to a growing crop, to an area where a crop is to be grown or to a domestic animal, a correspondingly combative or toxic amount, i.e. an insecticidally or acaricidally effective amount of the particular active compound of the invention alone or together with a carrier vehicle as noted above. The instant formulations or compositions are applied in the usual manner, for instance by spraying, atomizing, vaporizing, scattering, dusting, watering, squirting, sprinkling, pouring, fumigating, dressing, encrusting, and the like.

It will be realized, of course, that the concentration of the particular active compound utilized in admixture with the carrier vehicle will depend upon the intended application. Therefore, in special cases it is possible to go above or below the aforementioned concentration ranges.

The unexpected superiority and outstanding activity of the particular new compounds of the present invention are illustrated, without limitation, by the following examples:

EXAMPLE 1

Plutella test

Solvent: 3 parts by weight of dimethylformamide

Emulsifier: 1 part by weight of alkylaryl polyglycol ether

To produce a suitable preparation of active compound, 1 part by weight of the active compound was mixed with the stated amount of solvent containing the stated amount of emulsifier and the concentrate was diluted with water to the desired concentration.

Cabbage leaves (*Brassica oleracea*) were sprayed with the preparation of the active compound until dew moist and were then infested with caterpillars of the diamond-back moth (*Plutella maculipennis*).

After the specified periods of time, the degree of destruction was determined as a percentage: 100% means that all the caterpillars were killed, whereas 0% means that none of the caterpillars were killed.

The active compounds, the concentrations of the active compounds, the evaluation times and the results can be seen from the following Table:

Table 1

(Insects which damage plants)
*Plutella* test

| Active compounds | | Active compound concentration in % | Degree of destruction in % after 3 days |
|---|---|---|---|
| 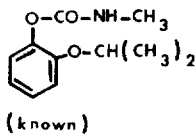 (known) (A) | | 0.1<br>0.01<br>0.001 | 100<br>90<br>0 |
| 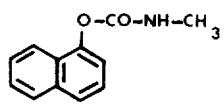 (known) (B) | | 0.1<br>0.01<br>0.001 | 100<br>60<br>0 |
| 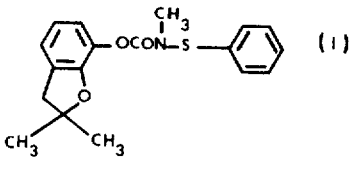 | (1) | 0.1<br>0.01<br>0.001 | 100<br>100<br>100 |
| 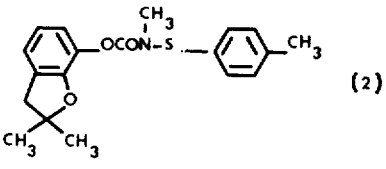 | (2) | 0.1<br>0.01<br>0.001 | 100<br>100<br>90 |
| 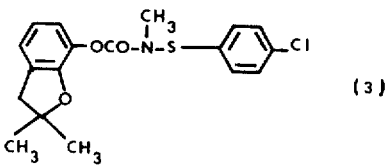 | (3) | 0.1<br>0.01<br>0.001 | 100<br>100<br>100 |
| 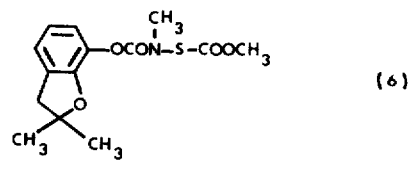 | (6) | 0.1<br>0.01<br>0.001 | 100<br>100<br>65 |
| 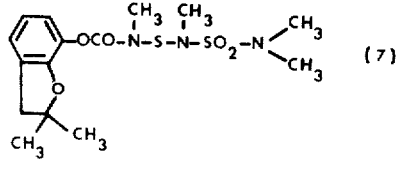 | (7) | 0.1<br>0.01<br>0.001 | 100<br>100<br>95 |

EXAMPLE 2

Myzus test (contact action)
Solvent: 3 parts by weight of dimethylformamide
Emulsifier: 1 part by weight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

Cabbage plants (*Brassica oleracea*) which had been heavily infested with peach aphids (*Myzus persicae*) were sprayed with the preparation of the active compound until dripping wet.

After the specified periods of time, the degree of destruction was determined as a percentage: 100% means that all the aphids were killed, whereas 0% means that none of the aphids were killed.

The active compounds, the concentrations of the active compounds, the evaluation times and the results can be seen from the following Table:

Table 2

(Insects which damage plants)
*Myzus* test

| Active compounds | Active compound concentration in % | Degree of destruction in % after 1 day |
|---|---|---|
| (A) (known) | 0.1<br>0.01<br>0.001 | 100<br>70<br>0 |
| (B) (known) | 0.1<br>0.01<br>0.001 | 100<br>45<br>0 |
| (1) | 0.1<br>0.01<br>0.001 | 100<br>100<br>100 |
| (2) | 0.1<br>0.01<br>0.001 | 100<br>100<br>100 |

EXAMPLE 3

Tetranychus test (resistant)
Solvent: 3 parts by weight of dimethylformamide
Emulsifier: 1 part by weight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

Bean plants (*Phaseolus vulgaris*), which had a height of approximately 10–30 cm, were sprayed with the preparation of the active compound until dripping wet. These bean plants were heavily infested with the two-spotted spider mite (*Tetranychus urticae*) in all stages of development.

After the specified periods of time, the effectiveness of the preparation of active compound was determined by counting the dead mites. The degree of destruction thus obtained was expressed as a percentage: 100% means that all the spider mites were killed whereas 0% means that none of the spider mites were killed.

The active compounds, the concentrations of the active compounds, the evaluation times and the results can be seen from the following Table:

Emulsifier 1 part by weight of alkylaryl polyglycol ether

To produce a suitable preparation of active compound, 1 part by weight of active compound was mixed with the stated amount of solvent, the stated amount of emulsifier was added and the concentrate was diluted with water to the desired concentration. The preparation of active compound was intimately mixed with the soil. The concentration of the active compound in the preparation was practically immaterial, the only decisive factor being the amount by weight of active compound per unit volume of soil, which is quoted in ppm (for example mg/l). The soil was filled into pots and the pots were left to stand at room temperature. After 24 hours the test insects were introduced into the treated soil and after a further 48 hours the degree of effectiveness of the active compound was determined in % by Table 3

| Active compounds | | (Mites which damage plants) *Tetranychus* test | |
|---|---|---|---|
| | | Active compound concentration in % | Degree of destruction in % after 2 days |
| 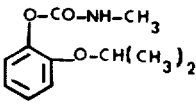 (known) (A) | | 0.1 | 0 |
| 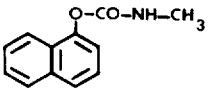 (known) (B) | | 0.1 | 0 |
| 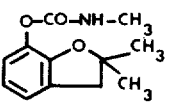 (known) (C) | | 0.1 | 0 |
| 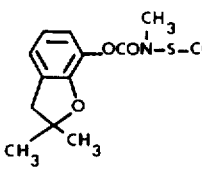 (6) | | 0.1 | 85 |

EXAMPLE 4

Critical concentration test/soil insects
Test insect: *Phorbia brassicae* grubs in the soil
Solvent: 3 parts by weight of acetone counting the dead and live test insects. The degree of effectiveness was 100% if all test insects had been killed and was 0% if exactly as many test insects were still alive as in the case of the control.

The active compounds, amounts used and results can be seen from the Table which follows:

Table 4

| Active compound | *Phorbia brassicae* grubs in the soil | | | | | |
|---|---|---|---|---|---|---|
| | Degree of destruction in % at an active-compound concentration in ppm of | | | | | |
| | 20 | 10 | 5 | 2.5 | 1.25 | 625 |
| 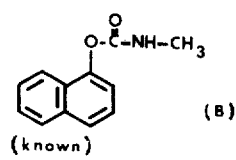 (known) | | | | | | 0 |

Table 4-continued

*Phorbia brassicae* grubs in the soil

| Active compound | Degree of destruction in % at an active-compound concentration in ppm of | | | | | |
|---|---|---|---|---|---|---|
| | 20 | 10 | 5 | 2.5 | 1.25 | 625 |
| 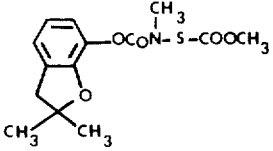 (6) | 100 | 100 | 100 | 100 | 50 | 0 |
| 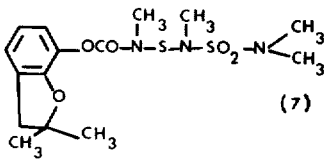 (7) | 100 | 100 | 100 | 50 | 0 | |
| 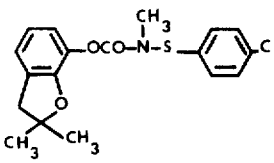 (3) | 100 | 100 | 100 | 100 | 90 | 50 |
| 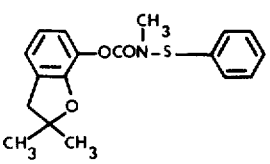 (1) | 100 | 100 | 100 | 100 | 98 | 50 |
| 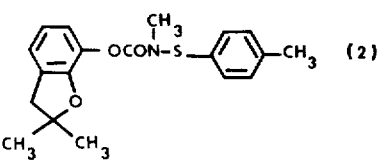 (2) | 100 | 100 | 100 | 50 | 0 | |

EXAMPLE 5

Mosquito larvae test
Test insects: *Aedes aegypti* (4th Larval stage)
Solvent: 99 parts by weight of acetone
Emulsifier: 1 part by weight of benzylhydroxydiphenylpolyglycol ether To produce a suitable preparation of active compound, 2 parts by weight of the active compound were dissolved in 1,000 parts by volume of the solvent containing the amount of emulsifier stated above. The solution thus obtained was diluted with water to the desired lower concentrations.

The aqueous preparations of the active compounds were placed in glass vessels and about 25 mosquito larvae were then placed in each glass vessel.

After 24 hours, the degree of destruction was determined as a percentage. 100% means that all the larvae were killed. 0% means that no larvae at all were killed.

The active compounds, the concentrations of the active compounds, the test insects and the results can be seen from the following Table:

EXAMPLE 6

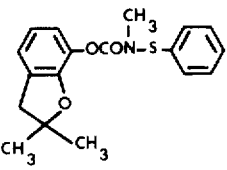
(1)

Table 5

| Active compound | Mosquito Larvae test Active-compound concentration of the solution in ppm | Degree of destruction in % |
|---|---|---|
| (C) (known) O-CO-NHCH₃ benzofuran | 10<br>1<br>0.1 | 100<br>100<br>0 |
| (1) OCON(CH₃)-S-phenyl benzofuran | 10<br>1<br>0.1 | 100<br>100<br>100 |
| (2) OCON(CH₃)-S-C₆H₄-CH₃ benzofuran | 10<br>1<br>0.1 | 100<br>100<br>95 |
| (3) OCO-N(CH₃)-S-C₆H₄-Cl benzofuran | 10<br>1<br>0.1<br>0.1<br>0.001 | 100<br>100<br>100<br>100<br>100 |
| (6) OCON(CH₃)-S-COOCH₃ benzofuran | 10<br>1<br>0.1 | 100<br>100<br>90 |
| (7) OCO-N(CH₃)-S-N(CH₃)-SO₂-N(CH₃)₂ benzofuran | 10<br>1<br>0.1 | 100<br>100<br>50 |

The process of the present invention is illustrated by the following preparative Examples.

Process (a): 8.2 g (0.05 mole) of 2,2-dimethylbenzofuranol-(7) and 9.3 g (0.05 mole) of N-methyl-N- phenylsulfenylcarbamic acid fluoride were dissolved in 200 ml of toluene. 6 g of triethylamine were then slowly added dropwise. After stirring for two hours at room temperature, the salt was filtered off, the filtrate was repeatedly washed with water and dried and the solvent was distilled off. The residue was a yellow oil. $n_D^{25}$: 1.5661.

Process (b): 22.1 g (0.1 mole) of 2,2-dimethyl-benzofuranyl (7)-N-methylcarbamate were suspended in 300 ml of toluene, and thereafter 14.5 g (0.1 mole) of phenylsulfenyl chloride were added. 11 g of triethylamine were slowly added dropwise while stirring vigorously. The mixture was then stirred for a further 2 hours at 30°C. The salt was then filtered off, the filtrate was twice washed with water and dried with $Na_2SO_4$ and the solvent was distilled off. A yellow oil remained.

The following were obtained by processes analogous to those described above:

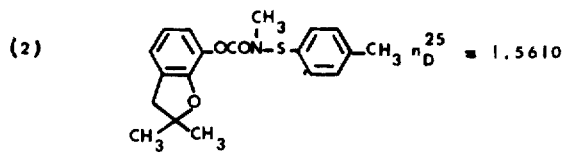

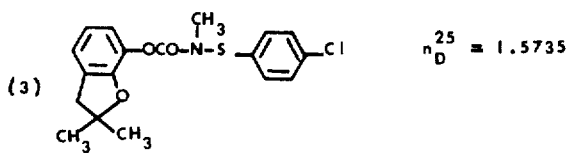

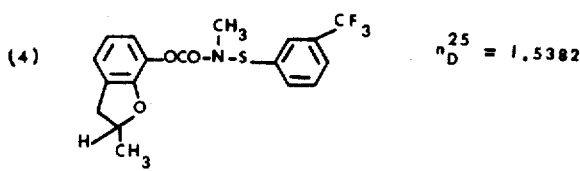

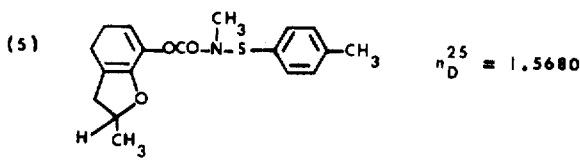

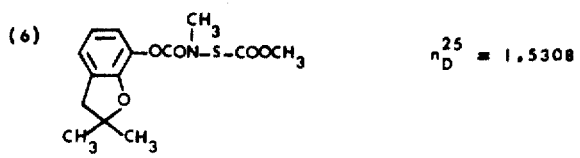

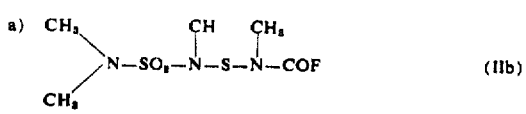

EXAMPLE 7

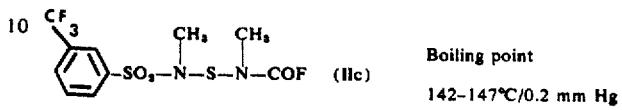

20.4 g (0.1 mole) of N,N,N'-trimethyl sulfonyl-diamido-N'-sulfenyl chloride and 7.7 g (0.1 mole) of N-methylcarbamic acid fluoride were dissolved in 200 ml of absolute toluene. 10 g of triethylamine were added dropwise, while stirring, the temperature not exceeding 40°C. The mixture was stirred for a further 2 hours at room temperature, the salt was filtered off and the filtrate was extracted by shaking with ice water, dried and distilled in vacuo. Boiling point = 137°C/0.2 mm Hg.

The following compound could be prepared analogously:

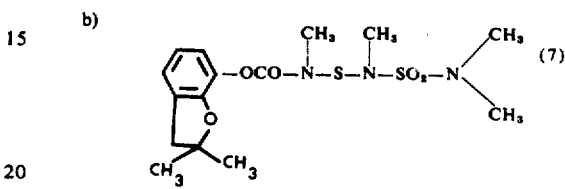

b)

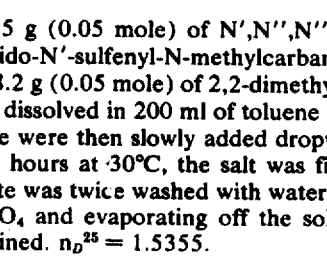

12.5 g (0.05 mole) of N',N'',N'''-trimethylsulfonyl-diamido-N'-sulfenyl-N-methylcarbamic acid fluoride and 8.2 g (0.05 mole) of 2,2-dimethylbenzofuranol-(7) were dissolved in 200 ml of toluene and 6 g of triethylamine were then slowly added dropwise. After stirring for 2 hours at 30°C, the salt was filtered off and the filtrate was twice washed with water. After drying with $Na_2SO_4$ and evaporating off the solvent, a yellow oil remained. $n_D^{25} = 1.5355$.

The following compounds could be prepared by analogous processes starting from known sulfenylated carbamic acid fluorides.

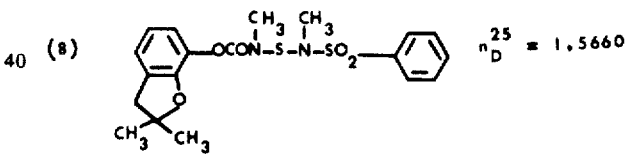

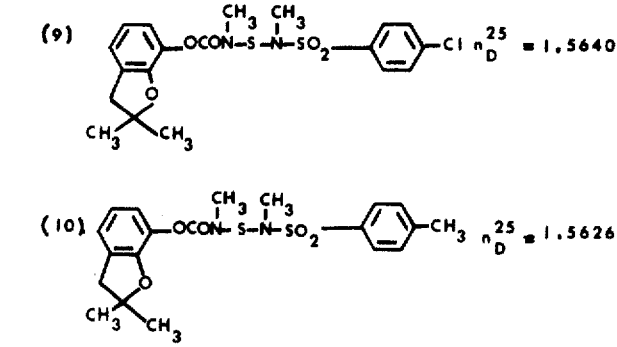

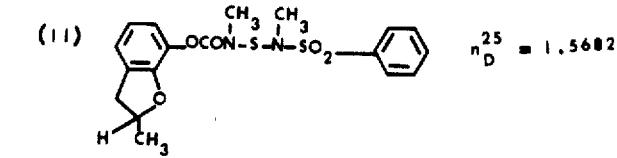

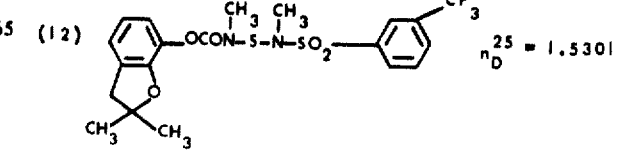

Other compounds which can be similarly prepared include:

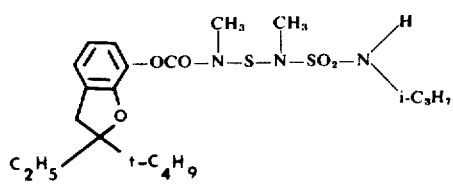

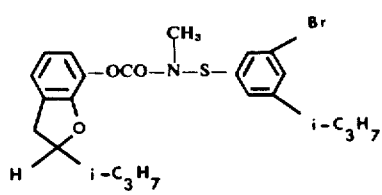

and the like.

It will be appreciated that the instant specification and examples are set forth by way of illustration and not limitation, and that various modifications and changes may be made without departing from the spirit and scope of the present invention.

What is claimed is:

1. An N-sulfenylated 2,3-dihydrobenzofuranyl-7-N-methylcarbamate of the formula

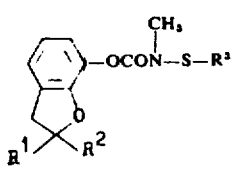

in which
 $R^1$ is hydrogen or $C_1$–$C_6$ alkyl,
 $R^2$ is $C_1$–$C_6$ alkyl, and
 $R^3$ is methoxycarbonyl; or the radical

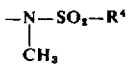

wherein
 $R_4$ is lower alkylamino, di-lower alkylamino, phenyl, or phenyl substituted by at least one of halogen, $C_1$–$C_6$ alkyl or trihalogenomethyl.

2. A compound according to claim 1, in which $R^1$ is hydrogen or methyl, $R^2$ is methyl, and $R^3$ is N,N',N'-trimethylsulfonyldiamido, N-methylbenzenesulfonamido, N-methyl-3-trifluoromethylbenzenesulfonamido, N-methyl-4-chlorobenzenesulfonamido or N-methyl-4-toluenesulfonamido.

3. The compound according to claim 1 wherein such compound is 2,2-dimethyl-2,3-dihydrobenzofuranyl-(7)-N-methoxycarbonylsulfenyl-N-methylcarbamate of the formula

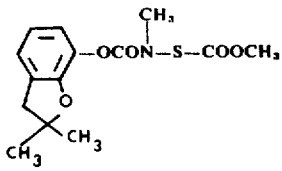

4. The compound according to claim 1 wherein such compound is 2,2-dimethyl-2,3-dihydrobenzofuranyl-(7)-N-(N',N'',N''-trimethylsulfonyldiamido-N'-sulfenyl)-N-methylcarbamate of the formula

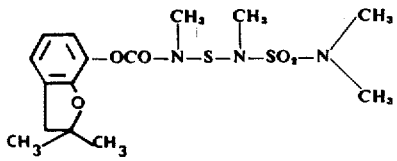

* * * * *